US012145900B2

(12) United States Patent
Favero et al.

(10) Patent No.: US 12,145,900 B2
(45) Date of Patent: Nov. 19, 2024

(54) PROCESS FOR FILTERING 2-ACRYLAMIDO-2-METHYLPROPANE SULFONIC ACID

(71) Applicant: SPCM SA

(72) Inventors: Cédrick Favero, Andrezieux Boutheon (FR); Raphaël Doudin, Andrezieux Boutheon (FR); Johann Kieffer, Andrezieux Boutheon (FR); Benoît Legras, Andrezieux Boutheon (FR)

(73) Assignee: SNF Group

( * ) Notice: Subject to any disclaimer, the term of this patent is extended or adjusted under 35 U.S.C. 154(b) by 537 days.

(21) Appl. No.: 17/609,173

(22) PCT Filed: May 7, 2020

(86) PCT No.: PCT/FR2020/050758
§ 371 (c)(1),
(2) Date: Nov. 5, 2021

(87) PCT Pub. No.: WO2020/229757
PCT Pub. Date: Nov. 19, 2020

(65) Prior Publication Data
US 2022/0227704 A1   Jul. 21, 2022

(30) Foreign Application Priority Data

May 15, 2019   (FR) ...................... 1905037

(51) Int. Cl.
*C07C 309/15*   (2006.01)
*B01D 33/073*   (2006.01)
(Continued)

(52) U.S. Cl.
CPC .......... *C07C 309/15* (2013.01); *B01D 33/073* (2013.01); *B01D 33/466* (2013.01);
(Continued)

(58) Field of Classification Search
CPC ... C07C 309/15; C07C 303/44; B01D 33/073; B01D 33/466; B01D 33/60; B01D 33/62; C08F 20/58; C09K 8/035
See application file for complete search history.

(56) References Cited

U.S. PATENT DOCUMENTS

| | | | |
|---|---|---|---|
| 6,448,347 B1 | 9/2002 | Quinn et al. | |
| 8,247,601 B2 | 8/2012 | Wakayama | |
| 2018/0244609 A1* | 8/2018 | Favero | ................ C07C 303/02 |

FOREIGN PATENT DOCUMENTS

| | | | | |
|---|---|---|---|---|
| GB | 1307240 A | * | 2/1973 | .......... B01D 33/067 |
| WO | WO-2009/072480 A1 | | 6/2009 | |

(Continued)

OTHER PUBLICATIONS

WO2017046546 (A1), SPCM SA, Method for producing the 2-acrylamido-2-methylpropane sulfonic acid monomer and polymer comprising said monomer, English translation, 11 pages (Year: 2017).*

(Continued)

*Primary Examiner* — Yate' K Cutliff
(74) *Attorney, Agent, or Firm* — Harris Beach PLLC

(57) ABSTRACT

A continuous process for filtering a suspension of 2-acrylamido-2-methylpropane sulfonic acid crystals by means of a rotary pressure filter equipped with a drum, a surface of which is provided with cells covered with a filter medium, the drum rotating within a fixed concentric cylinder comprising at least three zones sealed from each other, respectively a filtration zone, a washing zone and a discharge zone, each zone opening onto the cells.

20 Claims, 2 Drawing Sheets

(51) Int. Cl.
*B01D 33/46* (2006.01)
*B01D 33/60* (2006.01)
*B01D 33/62* (2006.01)
*C07C 303/44* (2006.01)
*C08F 20/58* (2006.01)
*C09K 8/035* (2006.01)

(52) U.S. Cl.
CPC ............ *B01D 33/60* (2013.01); *B01D 33/62* (2013.01); *C07C 303/44* (2013.01); *C08F 20/58* (2013.01); *C09K 8/035* (2013.01)

(56) References Cited

FOREIGN PATENT DOCUMENTS

WO    WO-2017046546 A1 *   3/2017  ........... C07C 303/02
WO    WO-2017/162545 A1   9/2017

OTHER PUBLICATIONS

PCT International Search Report and Written Opinion of the International Searching Authority for PCT/FR2020/050758 dated Jul. 5, 2020 (10 pages).

Demetra Dragan, "On the Ritter Synthesis of N-tert-Butylacrylamide (PartII)* Reaction between tert-Butylalcohol and Acrylonitrile in Non-aqueous Solvents" 1995, Irauian J. of Polymer Science and Technology, vol. 4 No. 1, (8 pages).

* cited by examiner

[Fig. 1]
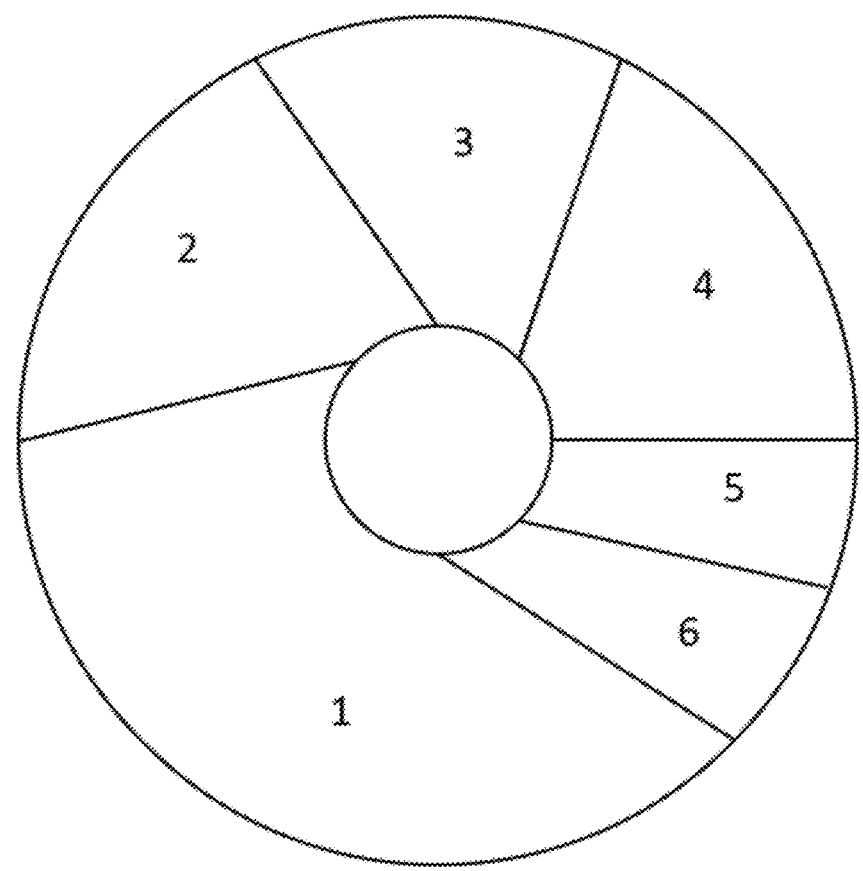

[Fig. 2]
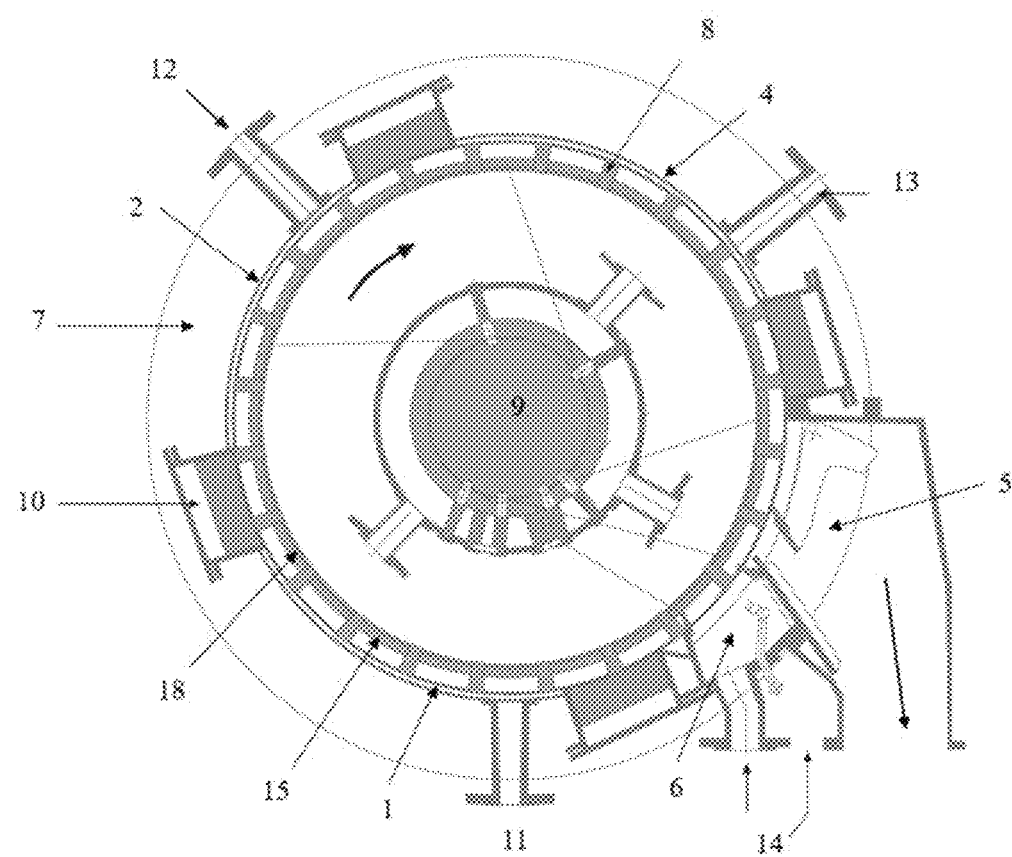

PROCESS FOR FILTERING 2-ACRYLAMIDO-2-METHYLPROPANE SULFONIC ACID

CROSS-REFERENCE TO RELATED APPLICATIONS

This application claims the benefit of French Patent Application No. 1905037, filed on May 15, 2019. The entirety of this application is incorporated herein by reference.

FIELD OF THE INVENTION

The field of the invention relates to the manufacture of a water-soluble sulfonated monomer, 2-acrylamido-2-methylpropane sulfonic acid (ATBS), and more precisely to a novel process for filtering a suspension of crystals of the 2-acrylamido-2-methylpropane sulfonic acid with a rotary pressure filter.

PRIOR STATE OF THE ART

The 2-acrylamido-2-methylpropane sulfonic acid is widely used as an additive in acrylic fibers, or as a raw material to obtain polymers used as a dispersant, hydrogel or thickener in various sectors such as the petroleum industry, construction, water treatment (seawater desalination, mineral industry, etc.) or cosmetics.

The reaction carried out in the process for preparing 2-acrylamido-2-methylpropane sulfonic acid corresponds to the reaction scheme below, in which acrylonitrile is present in excess so as to be both the solvent of the reaction and a reagent. The acrylonitrile is contacted with sulfuric acid and isobutylene.

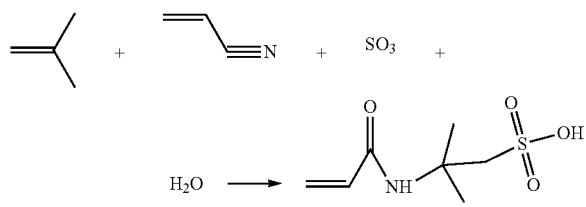

2-Acrylamido-2-methylpropane sulfonic acid is not soluble in the acrylonitrile solvent. Accordingly, the reaction product is in the form of a suspension of crystals in the reaction solvent.

By way of examples, U.S. Pat. No. 6,448,347 discloses a process for the manufacture of 2-acrylamido-2-methylpropane sulfonic acid in a continuous mode.

2-Acrylamido-2-methylpropane sulfonic acid is subsequently separated from the acrylonitrile, generally by filtration, and then dried. Drying of the 2-acrylamido-2-methylpropane sulfonic acid is necessary in order to decrease the amount of acrylonitrile and acrylamide remaining in the crystal. These two compounds being classified as carcinogenic component CMR, it is therefore necessary to carry out an effective filtration to remove the acrylonitrile, then dry it in order to obtain the lowest possible contents of acrylonitrile and acrylamide.

As described in the article entitled "On the Ritter synthesis of N-tert-butylacrylamide, reaction between tert-butylalcohol and acrylonitrile in non-aqueous system" published in the "Iranian J. of Polymer Science and Technology Vol 4 No. 1, 1995", the yield for the 2-acrylamido-2-methylpropane sulfonic acid is linked to the ratio of sulfur trioxide (SO3) free in the synthesis medium. In other words, the more the medium is sulfonating, the more the reaction is selective towards 2-acrylamido-2-methylpropane sulfonic acid to the detriment of N-tert-butylacrylamide.

In addition, in U.S. Pat. No. 8,247,601 which relates to a process for manufacturing 2-acrylamido-2-methylpropane sulfonic acid, it is explained that the IBSA impurities (2-methyl-2-propenyl-1-sulfonic acid) and IBDSA (2-methylidene-1,3-propylenedisulfonic acid) are by-products of the manufacturing process. The concentration of these two reaction by-products is proportional to the concentration of sulfur trioxide present in the reaction mixture.

Purification is necessary because impurities, even at low concentrations, originating from 2-acrylamido-2-methylpropane sulfonic acid strongly affect the polymerization, and the quality of the polymer obtained, more particularly its molecular weight and the rate of water-insoluble content.

In a first aspect, U.S. Pat. No. 8,247,601 discloses a control of the quantity of sulfur trioxide to be introduced into the reaction mixture based on on-line monitoring by liquid chromatography of the concentration of IBSA and IBDSA. In a second aspect, the 2-acrylamido-2-methylpropane sulfonic acid crystals undergo solid/liquid separation by centrifugation.

Patent WO2017/162545 discloses the use of a filtration or centrifugation technology for the solid/liquid separation of 2-acrylamido-2-methylpropane sulfonic acid crystals.

Continuous filtration technologies generally used include vacuum belt filters and solid or perforated bowl decanters.

Vacuum belt filters use the energy of the vacuum to create a vacuum between the suspension to be filtered and the filter cloth. Consequently, the filtration speed is limited by a depression of 1 bar (absolute vacuum). In addition, these filters are generally horizontal. Consequently, it is necessary to use a large floor zone per filtration unit.

Solid bowl decanters are continuous filtration technologies that use centrifugal force to separate a solid from a liquid. The product thus decanted is conveyed by a rotating screw in order to extract it from the equipment. As part of the crystal separation of 2-acrylamido-2-methylpropane sulfonic acid, the crystals cannot be washed in the solid bowl decanter. In addition, the residual moisture of the cake thus obtained is too high to allow the cake to be conveyed to the drying equipment. Finally, this residual moisture constitutes as much acrylonitrile as it is necessary to evaporate during the dryings step of the 2-acrylamido-2-methylpropane sulfonic acid crystals.

Perforated bowl decanters suffer from the same drawbacks as solid bowl decanters. It should be noted in passing that the minimum particle size for use of solid bowl decanters is 500 μm, while the 2-acrylamido-2-methylpropane sulfonic acid crystals have a D50 particle size generally around 100 μm. Consequently, the use of such technology would cause an important loss of crystals in the liquid filtrate.

There are also discontinuous filtration technologies, such as, for example, vertical and horizontal wringers, pressure filters, Nutsche filters, or the Universal filter (Gaudfrin brand).

Pressure filters use the supply pressure of the slurry as filtration energy by filling the filtration chambers. In order to improve the wringing of the cake thus formed, a membrane/diaphragm is used to compress the cake. It is known that this technology is not suitable in the context of compressible crystals, since this results in a reduction in the filtration rate and in the washing quality of this cake during a subsequent operation.

Vertical and horizontal wringers use centrifugal force to separate solid from liquid. It is frequent that after the initial filtration step, the washing of the cake is not carried out immediately, causing cracking of the surface of the cake and therefore preferential paths. Therefore, the washing step is not efficient because of these preferential paths, requiring an overconsumption of washing liquid to obtain the adequate quality. Vertical or horizontal wringers have relatively low batch cake production capacities, down to a few hundred kilograms.

Nutsche filters are cylindrical vessels with a filter cloth at the bottom. The suspension is supplied under pressure, and the set can be placed under vacuum. Given the dimensions of these filters, the thickness of the cake obtained is significant, up to several tens of centimeters. The filtration rate depends on the thickness of the cake. Consequently, the thicker the cake, the longer the filtration time is for the same filtration surface. In addition, Nutsche filters suffer from the same defect as horizontal or vertical wringers, namely the creation of preferential paths on the surface of the cake between the end of filtration and the start of the crystals washing step.

The Universal filter from Gaudfrin uses a set of vertical plates to filter a suspension which is contained in a stationary container. The trays are moved from one container to another in order to carry out the various filtration operations, washing and spinning operations. Unfortunately, the Gaudfrin universal filter requires as many containers as there are filtration, washing and drying steps. In addition, the filtration energy is obtained by depression with the vacuum between the suspension to be filtered and the interior of the fabric. Thus, the filtration speed is greatly reduced.

As document WO2009/072480 teaches us, the process for obtaining 2-acrylamido-2-methylpropane sulfonic acid should preferably be continuous in order to control the rate of the IBSA and IBDSA by-products by controlling the rate of sulfur trioxide in the reaction medium. Consequently, the set of discontinuous filters are not suitable and require the use of buffer storage. During these waiting times in buffer storage, the 2-acrylamido-2-methylpropane sulfonic acid crystals degrade over time. Without being bound by any theory, the acidity present in the reaction medium continues to generate IBSA and IBDSA by-products over time. In addition, given the low productivity per batch of discontinuous filters, it is necessary to increase the number of equipment to be installed in order to be able to filter the quantity produced by a continuous process for obtaining 2-acrylamido-2-acid. methylpropane sulfonic acid.

The applicant's WO2017/046546 document discloses the production of ATBS crystals and gives, by way of indication, different solid/liquid separation processes including the rotating drum filter, without indicating a preference for a process, nor without specifying the filtration parameters.

Document GB1307240 discloses a rotating drum filter for performing a solid/liquid separation of slurry, without defining any filtration parameter.

Therefore, there is a need to improve the processes for producing crystals of the existing 2-acrylamido-2-methylpropane sulfonic acid, with the objective of improving the purity of 2-acrylamido-2-methylpropane sulfonic acid, while offering a continuous process.

DISCLOSURE OF THE INVENTION

The applicant just discovered, surprisingly and unexpectedly, that the filtration of a suspension of 2-acrylamido-2-methylpropane sulfonic acid crystals by means of a rotary pressure filter makes it possible to achieve the aforementioned objectives.

The invention relates to a continuous process for filtering a suspension of 2-acrylamido-2-methylpropane sulfonic acid crystals by means of a rotary pressure filter provided with a drum on the surface of which at least one filtration step is carried out, said surface being provided with cells covered with a filter medium.

The present invention also relates to a process for manufacturing 2-acrylamido-2-methylpropane sulfonic acid comprising a step of manufacturing a suspension of 2-acrylamido-2-methylpropane sulfonic acid crystals, then a filtration step of said suspension with a rotary filter under pressure.

In addition, the present invention relates to a cake of 2-acrylamido-2-methylpropane sulfonic acid crystals obtained according to the process of the invention.

The invention also relates to a process for manufacturing 2-acrylamido-2-methylpropane sulfonic acid in the form of crystals from said cake.

The invention also relates to the polymers obtained from 2-acrylamido-2-methylpropane sulfonic acid crystals obtained according to the process of the invention, as well as the use of these polymers in oil and gas recovery, in water treatment, in sludge treatment, in papermaking, in construction, in the mining industry, in cosmetic formulation, in detergent formulation, in textile manufacturing or in agriculture.

More specifically, the invention relates to a continuous process for filtering a suspension of 2-acrylamido-2-methylpropane sulfonic acid crystals using a rotary pressure filter provided with a drum, the surface of which is provided with covered cells of a filter medium, said drum rotating within a fixed concentric cylinder comprising at least three zones sealed from each other, respectively a filtration zone, a washing zone and a discharge zone, each zone opening onto the cells, the process comprising the following steps:

a) supplying the filtration zone with a suspension of 2-acrylamido-2-methylpropane sulfonic acid crystals and filtering, preferably simultaneously, said suspension in the cells until a cake is formed, b) supplying the washing zone with a washing solution and washing, preferably simultaneously, the cake formed in the cells, c) discharging the washed cakes from the cells at the discharge zone.

According to the invention, the depth of the cells covering the filter medium is between 6 and 150 mm and a pressure of between 1 and 10 bars is applied in the filtration and washing zones.

In practice, the process comprises the following additional steps:

between step a) and b), simultaneously evacuating the filtrate resulting from the filtration, between step b) and c), simultaneously evacuating the filtrate resulting from the washing.

According to a preferred embodiment of the invention, in step b) the washing is carried out with a solution containing at least 90% by weight of acrylonitrile, and, more preferably, a solution consisting of acrylonitrile or a solution comprising from 90 to 99.9% by mass of acrylonitrile, and 0.1 to 10% by mass of water.

In a preferred embodiment, the process comprises at least one additional pressure washing step after step b) in a second washing zone, adjacent to the first, preferably at least two additional washing steps after step b), respectively in a second and a third washing zone adjacent to the first. In other words, the process according to the invention preferably comprises three successive washing steps.

In a preferred embodiment, the process comprises at least one of the following two additional steps:
 between step b) and step c), drying the washed cake by injecting gas into a drying zone;
 after step c), washing the cells before resuming a filtration cycle in a cleaning zone.

According to a preferred embodiment of the invention, in the drying step, the gas is at a temperature between 10° C. and 150, more preferably between 30 and 80° C. The gas is preferably an inert gas such as nitrogen.

The suspension of 2-acrylamido-2-methylpropane sulfonic acid crystals can be obtained according to all the processes for the manufacture of 2-acrylamido-2-methylpropane sulfonic acid leading to a suspension of crystals of 2-acrylamido-2-methylpropane sulfonic. The suspension preferably comprises between 10 and 30% by mass of 2-acrylamido-2-methylpropane sulfonic acid crystals, more preferably between 15 and 25% by mass.

The rotary pressure filter according to the invention generally comprises a rotating cylindrical drum, and a fixed concentric cylinder surrounding the drum, and is provided with several inlets or zones, generally an inlet for the suspension to be filtered, an inlet for the washing solution, an inlet for the drying gas, an inlet for the cleaning solution, and an outlet for discharging the filtered material.

In the present invention, the expression "rotary pressure filter" is used to denote the apparatus used for filtration, and generally comprising the aforementioned elements. In other words, the expression "rotary pressure filter" is not limited only to the drum provided with cells covered with a filter medium, but does relate to the apparatus as a whole.

Cells are arranged over the entire surface of the rotating drum. They have a face open to the outside of the drum thus making it possible to receive the suspension of crystals, and an inner face provided with a filter.

According to an essential characteristic of the invention, the depth of the cells is between 6 and 150 mm, preferably between 10 and 100 mm, more preferably between 15 and 70 mm, even more preferably between 20 and 70 mm, even more preferably between 30 and 60 mm.

The liquid and gaseous effluents are evacuated from the rotary filter by any known means. It may be a single pipe located in practice in the center of the drum and receiving all the effluents or individual pipes each receiving a type of effluent.

When the process according to the invention comprises at least two washing steps, the effluents coming from each of the washing zones may be collected separately or collectively. One or more effluents, collected separately or collectively, may be used for subsequent washing. In other words, an effluent may be used as a washing solution.

In a particular mode according to the invention, during the washing step, and when the process comprises at least two washing steps, the cake present in the rotary filter is washed in a co-current or counter-current mode.

In the co-current mode, at least one effluent from a washing zone n−1 is used as a washing solution for a washing zone n. For example, in the case of a process comprising three washing zones, the effluent from the first washing zone is used as the washing solution in the second washing zone, and the effluent from the second washing zone is used as the washing solution in the third washing zone.

In a countercurrent mode, at least one effluent from an n+1 washing zone is used as a washing solution from an n washing zone. For example, in the case of a process comprising three washing zones, the effluent from the third washing zone is used as the washing solution in the second washing zone, and the effluent from the second washing zone is used as a washing solution in the first washing zone. Preferably, the washing solution used in the last washing zone is a so-called "clean" solution, i.e., not yet used for washing, and preferably a solution containing at least 90% by weight of acrylonitrile, and more preferably a solution consisting of acrylonitrile or a solution comprising from 90 to 99.9% by mass of acrylonitrile, and 0.1 to 10% by mass of water. The counter-current mode is preferred.

The size of the filter cells, otherwise called the mesh opening, is preferably between 1 and 500 µm, more preferably between 5 and 250 µm.

In a preferred embodiment of the invention, the concentric fixed cylinder comprises:
 a filtration zone (1) comprising an inlet through which the drum cells are supplied under pressure with a suspension of 2-acrylamido-2-methylpropane sulfonic acid crystals,—a washing zone (2) comprising an inlet through which the drum cells are supplied under pressure with a washing solution,
 optionally at least, a second washing zone (3) comprising an inlet through which the drum cells are supplied under pressure with a washing solution,
 a drying zone (4) comprising an inlet through which the drum cells are supplied under pressure with gas,
 a discharge zone (5) comprising a scraper and allowing the evacuation of the cake from the cells,
 a cleaning zone (6) comprising an inlet through which the cells are supplied with a cleaning solution, each zone being separated from the other zones by a separation means, making it possible to guarantee a seal between the different zones.

In a preferred embodiment of the invention, the concentric fixed cylinder comprises a second washing zone, and preferably a third washing zone. The washing zones are positioned one after the other, the first washing zone being positioned after the filtration zone, and the last washing zone being positioned before the drying zone.

The suspension of 2-acrylamido-2-methylpropane sulfonic acid crystals is introduced, continuously and under pressure, into the filtration zone, then the suspension becomes lodged in the cells in order to be filtered under the pressure applied. Part of the liquid is then extracted from the cells and evacuated.

When pressure is applied, it is applied from the outside of the fixed cylinder towards the interior of the fixed cylinder. The cake remains in the cells throughout the process, until it is extracted in the discharge zone.

While the cylindrical drum is in motion, the cells change zone to enter the washing zone into which a washing solution is injected under applied pressure, preferably a solution containing at least 90% by weight of acrylonitrile. In the same way, liquid is then extracted from the cells and discharged.

Optionally, the cells enter at least a second washing zone and follow the same process as in the first.

The cells then enter the drying zone into which a gas is injected under pressure. The gas is preferably hot, preferably having a temperature between 10° C. and 150° C., more preferably between 30 and 80° C. The gas is generally an inert gas such as nitrogen. The gas charged with acrylonitrile is evacuated to a condenser in order to recover the acrylonitrile, the latter being recycled in the process for manufacturing 2-acrylamido-2-methylpropane sulfonic acid.

Finally, the cells enter the discharge zone for discharging the crystal cake thus obtained. The discharging of the crystal cake is preferably carried out with a scraper allowing the cake to be extracted from the cells. Pressure in the opposite direction, i.e., from the inside to the outside of the cylinder, is preferably applied in this zone, thus allowing the cake to be properly discharged. The gas used is generally nitrogen.

The cells are then optionally cleaned in the cleaning zone with a solvent. Generally, the solvent is a solution containing at least 90% by weight of acrylonitrile. The solvent is then extracted. The cells are then ready to be recharged in crystal suspension in the filtration zone. A pressure of between 1 and 10 bars is advantageously applied in the cleaning zone.

The rotational speed of the drum is preferably between 2 and 60 revolutions per minute, more preferably between 5 and 40 revolutions per minute.

The pressure systematically applied in the filtration, washing and drying zones, optionally for the others (discharge zone, cleaning zone) is between 1 to 10 bars, pressure which may be different from one zone to another, or from one step to another. The pressure applied is preferably between 1.1 and 9, preferably between 1.5 and 9, more preferably between 2 and 7 bars.

In a preferred embodiment according to the invention, the pressure is different from one zone to another, or from one step to another.

In this preferred embodiment, the pressure applied in the filtration zone of the rotary filter is between 1 and 10 bars, preferably between 1.1 and 9, more preferably between 1.5 and 7, even more preferably between 1.5 and 5, even more preferably between 2 and 4 bars.

In this preferred embodiment, the pressure applied in the washing zone of the rotary filter is between 1 and 10 bars, preferably between 1.1 and 9, more preferably between 1.5 and 9, even more preferably between 2 and 8, even more preferably between 3 and 7 bars.

In this preferred embodiment, the pressure applied in the drying zone of the rotary filter is between 1 and 10 bars, preferably between 1.1 and 10, more preferably between 2 and 10 bars, even more preferably between 3 and 10, even more preferably between 4 and 10 bars.

The supply rate of the suspension of 2-acrylamido-2-methylpropane sulfonic acid crystals in the filtration zone is between 1 m$^3$/h and 30 m$^3$/h.

The drum preferably has a diameter of between 0.5 m and 2.5 m, and a length of between 0.1 m and 3 m.

The invention also relates to a process for manufacturing 2-acrylamido-2-methylpropane sulfonic acid comprising a filtration step with a rotary pressure filter as described above. The suspension of 2-acrylamido-2-methylpropane sulfonic acid crystals may be obtained according to all the processes for the manufacture of 2-acrylamido-2-methylpropane sulfonic acid leading to a suspension of 2-acrylamido-2-methylpropane sulfonic acid crystals.

The invention also relates to a cake of 2-acrylamido-2-methylpropane sulfonic acid crystals obtained according to the process of the invention. This crystal cake is highly concentrated in 2-acrylamido-2-methylpropane sulfonic acid crystals. Preferably, the concentration of 2-acrylamido-2-methylpropane sulfonic acid crystals is between 75 and 99% by mass. The crystal cake obtained also contains very little acrylonitrile, IBSA and IBDSA. Preferably, the cake of 2-acrylamido-2-methylpropane sulfonic acid crystals contains less than 25% by weight of acrylonitrile, more preferably less than 20% by weight of acrylonitrile.

The cake preferably contains less than 100 ppm of IBSA and less than 10 ppm of IBDSA, more preferably less than 70 ppm of IBSA and less than 70 ppm of IBDSA, still more preferably strictly less than 60 ppm of IBSA and strictly less than 60 ppm of IBDS, even more preferably less than 55 ppm of IBSA and less than 55 ppm of IBDSA, even more preferably less than 50 ppm of IBSA and less than 50 ppm of IBDSA, even more preferably less than 40 ppm of IBSA and less of 40 ppm of IBDSA. The IBSA and IBDSA impurity levels are measured by liquid chromatography, for example according to the following process: ODS-3 column produced by GL Science, eluent: 0.03% trifluoroacetic acid/acetonitrile solution, eluent flow rate: 0.8 ml/min, and detector wavelength: 200 nm.

The invention also relates to a process for producing 2-acrylamido-2-methylpropane sulfonic acid in the form of crystals from said cake by drying. In practice, the crystal cake is generally dried in a dryer to obtain crystals in powder form. Generally, following the drying step, the concentration of acrylonitrile in the crystals is less than 1000 ppm.

Another aspect of the invention relates to the use of 2-acrylamido-2-methylpropane sulfonic acid crystals obtained according to the process of the invention for the manufacture of copolymers. This aspect of the invention also covers the use of 2-acrylamido-2-methylpropane sulfonic acid salts.

The invention also relates to a polymer obtained from 2-acrylamido-2-methylpropane sulfonic acid crystals obtained according to the process of the invention. Since the crystals have an extremely high purity, the polymers thus obtained exhibit improved performance.

Indeed, the polymers obtained from the 2-acrylamido-2-methylpropane sulfonic acid crystals according to the process of the invention have a higher molecular weight. In addition, the polymers do not exhibit insoluble particles when they are dissolved. Generally, the 2-acrylamido-2-methylpropane sulfonic acid crystals are placed in aqueous solution before being used to make polymers.

According to a particular embodiment of the invention, the polymer is a homopolymer of 2-acrylamido-2-methylpropane sulfonic acid.

According to another particular embodiment of the invention, the polymer is a copolymer comprising 2-acrylamido-2-methylpropane sulfonic acid obtained according to the process of the invention, and at least one water-soluble monomer.

The water-soluble monomer may be a nonionic monomer which may, in particular, be chosen from the group comprising water-soluble vinyl monomers, and particularly acrylamide; N-isopropylacrylamide; N, N-dimethylacrylamide; N-vinylformamide; acryloyl morpholine; N, N-diethyl acrylamide; N-tert-butyl acrylamide; N-tert-octylacrylamide; N-vinylpyrrolidone; N-vinyl caprolactam; N-vinylimidazole, hydroxyethyl methacrylamide, hydroxypropylacrylate, isoprenol and diacetone acrylamide. Advantageously, the nonionic monomer is acrylamide.

The water-soluble monomer may also be chosen from the group of anionic monomers. The anionic monomer(s) which may be used within the framework of the invention may be chosen from a large group. These monomers may have acrylic, vinyl, maleic, fumaric, malonic, itaconic, allylic functions and contain a carboxylate, phosphonate, phosphate, sulfate, sulfonate or other group with an anionic charge. The anionic monomer may be in acid form or alternatively in the form of an alkaline earth metal salt, an alkali metal salt or an ammonium salt. Examples of suitable monomers include acrylic acid; methacrylic acid; itaconic acid; crotonic acid; maleic acid; fumaric acid; monomers of strong acid type exhibiting, for example, a function of sulfonic acid or phosphonic acid type, such as vinylsulfonic acid, vinylphosphonic acid, allylsulfonic acid, methallylsulfonic acid, 2-methylidenepropane-1 acid, 3-disulfonic acid, 2-sulfoethylmethacrylate, sulfopropylacrylate, allylphosphonic acid, styrene sulfonic acid; and the water-soluble salts of these monomers such as their alkali metal, alkaline earth metal, or ammonium salts.

The water-soluble monomer may be a cationic monomer of acrylamide, acrylic, vinyl, allylic or maleic type having an amine or quaternary ammonium function. Mention may be made, in particular and without limitation, of dimethylaminoethyl acrylate (DMAEA), and dimethylaminoethyl methacrylate (DMAEMA) quaternized or salified, dimethyldiallylammonium chloride (DADMAC), acrylamido propyltrimethyl ammonium chloride (APTAC) and methacrylamido propyltrimethyl ammonium chloride (MAPTAC).

The water-soluble monomer can be a zwitterionic monomer such as derivatives having an acrylamide, acrylic, vinyl, allylic or maleic unit, and having an amine or quaternary ammonium function and an acid function of the carboxylic (or carboxylate), sulfonic (or sulfonate) type. or phosphoric (or phosphate). Mention may be made, such as 2-((2-(acryloyloxy)ethyl) dimethylammonio) ethane-1-sulfonate, 3-((2-(acryloyloxy) ethyl)dimethylammonio) propane-1-sulfonate, 4-((2-(acryloyloxy)ethyl) dimethylammonio) butane-1-sulfonate, [2-(acryloyloxy) ethyl] (dimethylammonio) acetate, derivatives of dimethylaminoethyl methacrylate such as 2-((2-(methacryloyloxy) ethyl) dimethylammonio) ethane-1-sulfonate, 3-((2-(methacryloyloxy) ethyl) dimethylammonio) propane-1-sulfonate, 4-((2-(methacryloyloxy) ethyl) dimethylammonio) butane-1-sulfonate, [2-(methacryloyloxy) ethyl] (dimethylammonio) acetate, derivatives of dimethylamino propylacrylamide such as 2-((3-acrylamidopropyl) dimethylammonio) ethane-1-sulfonate, 3-((3-acryl amidopropyl) dimethylammonio) propane-1-sulfonate, 4-((3-acrylamidopropyl) dimethylammonio) butane-1-sulfonate, [3-(acryloyloxy) propyl] (dimethylammonio) acetate, derivatives of dimethylamino propyl methylacrylamide such as 2-((3-methacrylamidopro)pyl) dimethylammonio) ethane-1-sulfonate, 3-((3-methacryl amidopropyl) dimethylammonio) propane-1-sulfonate, 4-((3-methacrylamidopropyl) dimethylammonio) butane-1-sulfonate and [3-(methacryloyloxy)propyl] (dimethylammonio) acetate.

According to the invention, the copolymer may have a linear, branched, crosslinked, star (star-shaped) or comb (comb-shaped) structure. These structures may be obtained by selecting the initiator, the transfer agent, or the polymerization technique such as controlled radical polymerization known as Reversible-Addition Fragmentation chain Transfer (RAFT), Nitroxide Mediated Polymerization (NMP) or by Atom Transfer Radical Polymerization (ATRP), incorporation of structural monomers, concentration.

In general, the copolymer does not require the development of a particular polymerization process. Indeed, it can be obtained according to all the polymerization techniques well known to a person skilled in the art. It may, in particular, be solution polymerization; gel polymerization; precipitation polymerization; (aqueous or inverse) emulsion polymerization; suspension polymerization; reactive extrusion polymerization; or micellar polymerization.

According to a particular embodiment of the invention, the copolymer may be post hydrolyzed. Post-hydrolysis is the reaction of the copolymer after polymerization. This step consists of the reaction of the hydrolyzable functional groups of the nonionic monomers, such as the amide or ester functions, with a base. During this post-hydrolysis step of the copolymer, the number of carboxylic acid functions increases. Indeed, the reaction between the base and the amide or ester functions present in the copolymer produces carboxylate groups.

The copolymer may be in liquid, gel or solid form when its preparation includes a drying step such as spray drying, drying on a drum, drying by electromagnetic radiation (high-frequency microwave) or else drying in a fluidized bed.

The copolymer may have a molecular weight between 10,000 and 30 million daltons. It may be a dispersant, a flocculant or a superabsorbent.

The copolymer preferably contains at least 10 mol % of 2-acrylamido-2-methylpropane sulfonic acid obtained according to the process of the invention, preferentially at least 30 mol %, more preferably at least 50 mol %.

The invention also relates to the use of the polymer obtained from 2-acrylamido-2-methylpropane sulfonic acid crystals obtained according to the process of the invention, in oil and gas recovery, in water treatment, in sludge treatment, in papermaking, in construction, in the mining industry, in cosmetic formulation, in detergent formulation, in textile manufacturing or in agriculture.

Oil and gas recovery processes are generally treatments of subterranean formations in which a polymer is used to increase the viscosity of the aqueous injection fluid and/or reduce the level of frictional resistance that occurs during injection of said fluid into a subterranean formation, or even to, punctually or definitively, plug a part of the subterranean formation.

These subterranean treatments include, but are not limited to, drilling operations, stimulation treatments such as fracturing operations, completion operations and the improved process of oil recovery by flushing with a polymer solution.

The invention also related to the use of the polymer obtained from 2-acrylamido-2-methylpropane sulfonic acid crystals obtained according to the process of the invention, in particular as a flocculant, dispersant, thickening agent, absorbing agent or friction reducing agent.

The invention, and the advantages which result therefrom, will emerge more clearly from the following figures and examples given, in a non-limiting manner, in order to illustrate the invention.

DESCRIPTION OF THE FIGURES

FIG. 1 schematically represents the different zones of the rotary pressure filter.

FIG. 2 schematically represents the various elements of a rotary pressure filter according to the invention.

More precisely, FIG. 1 represents a simplified cross section of the rotary pressure filter according to the invention showing the filtration zone (1), a first washing zone (2), a second washing zone (3), a drying zone (4), a discharge zone (5), and a cleaning zone (6).

More precisely, FIG. 2 represents a cross section of a rotary filter according to the invention not comprising a second washing zone (6). The rotary filter according to the invention comprises a fixed cylindrical casing (7), itself comprising a filtration zone (1), a washing zone (2), a drying zone (4), a discharge zone (5), and a cleaning zone (6). It also includes a rotating drum (8) and a central axis (9). The cylindrical casing comprises sealed separation elements for each zone (10), an inlet for the suspension to be filtered (11), an inlet for washing (12), an inlet for drying (13), a discharge zone (5), and an inlet for cleaning (14). The rotating drum comprises cells (15) provided with a filter (16).

EXAMPLARY EMBODIMENTS OF THE INVENTION

Example 1—Production of Crystal Suspensions of 2-Acrylamido-2-Methylpropane Sulfonic Acid Several ATBS crystal suspensions are produced according to the operating conditions detailed in Table 1.

Acrylonitrile and sulfuric acid are continuously added into a first 1,000-liter stainless steel reactor.

This first reaction mixture is cooled to a temperature of −10° C.

A second 10,000-liter reactor is continuously supplied with the mixture described above, as well as with isobutylene. The temperature of this mixture is maintained at a given temperature, called the mixing temperature.

The crystal suspensions A to G of 2-acrylamido-2-methylpropane sulfonic acid are thus obtained.

TABLE 1

Operating conditions for obtaining ATBS crystal suspensions A to G.

| ATBS crystal suspension | Acrylonitrile flow rate (kg/h) | H2SO4 concentration (%) | H2SO4 flow rate (kg/h) |
|---|---|---|---|
| A | 7586 | 101.13 | 927 |
| B | 3833 | 101.9 | 404 |
| C | 3000 | 99 | 443 |
| D | 3907 | 102.6 | 374 |
| E | 3231 | 99.8 | 498 |
| F | 2482 | 101.5 | 339 |
| G | 6546 | 102.2 | 750 |

| ATBS crystal suspension | Isobutylene flow rate (kg/h) | Mixture temperature (° C.) | Residence time in the 10 m$^3$ reactor (h) | Suspended solids rate |
|---|---|---|---|---|
| A | 487 | 45 | 1.1 | 20 |
| B | 261 | 43 | 2.2 | 21.5 |
| C | 279 | 44 | 2.7 | 27.7 |
| D | 219 | 40 | 2.2 | 18 |
| E | 270 | 40 | 2.5 | 25 |
| F | 178 | 38 | 3.3 | 22 |
| G | 247 | 41 | 1.3 | 20 |

In the following filtration examples, the size of the filters is adapted according to the flow rate which supplies the filter, itself depending on the raw material flow rates, the aim being to have a continuous process. Indeed, in Table 1, depending on the residence times in the 10 m$^3$ reactor, the sum of the acrylonitrile, sulfuric acid and isobutylene flow rates is proportionally variable.

As such, in the following filtration examples, a filtration rate in kg of 2-acrylamido-2-methylpropane sulfonic acid per hour and per square meter of filtration surface is recalculated.

Filtration flow rate (kg/h/m$^2$)=supply flow rate (kg/h)/filtration surface (m$^2$)

Example 2—Filtration with a Rotating Pressurized Filter

The ATBS crystal suspensions A to G produced in Example 1 are supplied into the filtration zone of the rotary filter described above, and therefore the cells of the opposite drum. The suspension is supplied under pressure in order to subject the suspension to filtration.

Several series of tests are carried out. In the first five series, the supply pressure, also called the filtration pressure, the washing pressure and the drying pressure are different from each other. In a sixth series of tests, these pressures are identical to each other. In a seventh series of tests, the depth of the filtration cells is varied.

A) Different Pressures According to the Zones

In the first series of tests, the filter supply pressure is 7 bars. This pressure corresponds to the pressure applied in the filtration zone.

The rotating drum has a rotational speed of 30 revolutions per minute. The filtration cells have a depth of 50 mm and are covered by a polypropylene filter cloth with a mesh opening of 50 μm.

The cake formed in each of the filtration cells is then conveyed to the washing zone.

A washing solution, at a pressure of 1.5 bar, containing 95% by mass of acrylonitrile and 5% by mass of water supplies the washing zone of the rotary filter.

A nitrogen gas stream, at a pressure of 2 bars, supplies the drying zone of the rotary filter.

The cake thus washed and dried is then conveyed to the discharge zone. Pressurized nitrogen is applied from inside the drum in order to discharge the cake. In addition, a knife is inserted inside the cell to help scrape the cake. The cake obtained has residual moisture in acrylonitrile. An analysis by liquid chromatography of the crystals obtained makes it possible to complete the residual contents of IBSA and IBDSA.

The experimental conditions of the filtration tests of the suspensions A to G are recorded in Table 2. The analysis results on the cakes obtained are recorded in Table 3.

TABLE 2

Experimental filtration conditions for suspensions A to G with rotary pressure filter technology.

| Filtration test | ATBS crystal suspension | Supply rate (kg/h) | Filter surface (m$^2$) | Filtration rate (kg/h/m$^2$) | Supply pressure (bars) |
|---|---|---|---|---|---|
| 1 | A | 9000 | 14.4 | 625 | 7 |
| 2 | B | 4500 | 7 | 643 | 7 |
| 3 | C | 3720 | 5.6 | 664 | 7 |
| 4 | D | 4500 | 8 | 562 | 7 |
| 5 | E | 4000 | 6.8 | 588 | 7 |
| 6 | F | 3000 | 5 | 600 | 7 |
| 7 | G | 7550 | 12.5 | 604 | 7 |

TABLE 3

Analysis results on the cakes obtained with the rotary filter technology with a 7-bar supply pressure of the filtration zone.

| Filtration test | ATBS crystal suspension | Moisture of crystals obtained (%) | IBSA (ppm) | IBDSA (ppm) |
|---|---|---|---|---|
| 1 | A | 23 | 55 | 59 |
| 2 | B | 22 | 53 | 62 |
| 3 | C | 21 | 51 | 52 |
| 4 | D | 24 | 58 | 64 |
| 5 | E | 22 | 59 | 58 |
| 6 | F | 23 | 51 | 59 |
| 7 | G | 24 | 62 | 64 |

In the second and third series of tests, the conditions are identical to those of the first series, except that the only parameter which changes is that of the supply pressure of the filter, i.e., the pressure applied in the filtration zone. Tables 4 and 5 summarize the results obtained respectively with a filter supply pressure of 5 bars (second series) and 2.5 bars (third series).

TABLE 4

Analysis results on the cakes obtained with the rotary filter technology with a 5-bar supply pressure of the filtration zone.

| Filtration test | ATBS crystal suspension | Moisture of crystals obtained (%) | IBSA (ppm) | IBDSA (ppm) |
|---|---|---|---|---|
| 1 | A | 21 | 52 | 57 |
| 2 | B | 19 | 49 | 56 |
| 3 | C | 19 | 48 | 49 |
| 4 | D | 20 | 52 | 58 |
| 5 | E | 19 | 51 | 54 |
| 6 | F | 20 | 46 | 54 |
| 7 | G | 22 | 54 | 59 |

TABLE 5

Analysis results on the cakes obtained with the rotary filter technology with a 2.5-bar supply pressure of the filtration zone.

| Filtration test | ATBS crystal suspension | Moisture of crystals obtained (%) | IBSA (ppm) | IBDSA (ppm) |
|---|---|---|---|---|
| 1 | A | 18 | 48 | 49 |
| 2 | B | 17 | 49 | 49 |
| 3 | C | 18 | 43 | 43 |
| 4 | D | 18 | 46 | 48 |
| 5 | E | 17 | 45 | 47 |
| 6 | F | 19 | 42 | 46 |
| 7 | G | 20 | 46 | 46 |

These results show that the IBSA and IBDSA impurity levels decrease when the pressure in the filtration zone goes from 7 bars to 5 bars then to 2.5 bars. This shows that an adjustment of the pressure in the filtration zone makes it possible to obtain a better purity of ATBS.

In a fourth series of tests, the same ATBS crystal suspensions A to G are supplied into the same rotating drum filter. The filtration conditions remain the same but the pressures applied are as follows. The supply pressure in the filtration zone is 7 bars, the pressure in the washing zone is 4 bars, and the pressure in the drying zone is 8 bars.

The analysis results on the cakes obtained are given in Table 6.

TABLE 6

Analysis results on the cakes obtained with the rotary filter technology with a 7-bar supply pressure in the filtration zone, a 4-bar washing pressure and an 8-bar drying pressure.

| Filtration test | ATBS crystal suspension | Moisture of crystals obtained (%) | IBSA (ppm) | IBDSA (ppm) |
|---|---|---|---|---|
| 1 | A | 15 | 40 | 45 |
| 2 | B | 16 | 38 | 47 |
| 3 | C | 14 | 30 | 38 |
| 4 | D | 18 | 42 | 48 |
| 5 | E | 16 | 43 | 43 |
| 6 | F | 18 | 35 | 42 |
| 7 | G | 19 | 48 | 48 |

These results show that by adjusting the pressures in the washing zone and in the drying zone, respectively to 4 bars and 8 bars, the IBSA and IBDSA impurity levels further decrease compared to the previous tests, demonstrating the possibility to obtain higher purity ATBS crystals.

A fifth series of tests is carried out in which the same ATBS crystal suspensions A to G are supplied into the same rotating drum filter. The filtration conditions remain the same, but the pressures applied are as follows. The supply pressure in the filtration zone is 2.5 bars, the pressure in the washing zone is 4 bars, and the pressure in the drying zone is 8 bars.

The analysis results on the cakes obtained are shown in Table 7.

TABLE 7

Analysis results on the cakes obtained with the rotary filter technology with a 2.5-bar supply pressure in the filtration zone, a 4-bar washing pressure and an 8-bar drying pressure.

| Filtration test | ATBS crystal suspension | Moisture of crystals obtained (%) | IBSA (ppm) | IBDSA (ppm) |
|---|---|---|---|---|
| 1 | A | 13 | 37 | 39 |
| 2 | B | 15 | 36 | 40 |
| 3 | C | 13 | 30 | 35 |
| 4 | D | 17 | 38 | 40 |
| 5 | E | 15 | 39 | 39 |
| 6 | F | 17 | 35 | 39 |
| 7 | G | 17 | 39 | 40 |

These results show that the choice of different and appropriate pressures in each of the zones makes it possible to obtain very low levels of IBSA and IBDSA impurities and, therefore, very high purity ATBS crystals.

B) Constant Pressures in the Zones

A sixth series of tests is carried out in which the same ATBS crystal suspensions A to G are supplied into the same rotating drum filter. The filtration conditions remain the same but the pressures applied are as follows. The supply pressure, also called the pressure in the filtration zone, the washing pressure and the drying pressure are equal to 2 bars.

The analysis results on the cakes obtained are shown in Table 8.

TABLE 8

Analysis results on the cakes obtained with the rotary filter technology with a pressure in the filtration, washing and drying zone equal to 2 bars.

| Filtration test | ATBS crystal suspension | Moisture of crystals obtained (%) | IBSA (ppm) | IBDSA (ppm) |
|---|---|---|---|---|
| 1 | A | 18 | 44 | 47 |
| 2 | B | 17 | 47 | 46 |
| 3 | C | 18 | 40 | 40 |
| 4 | D | 18 | 42 | 45 |
| 5 | E | 17 | 42 | 45 |
| 6 | F | 19 | 41 | 43 |
| 7 | G | 20 | 43 | 45 |

C) Variation in Cell Depth

Finally, a seventh and final series of tests is carried out by varying the depth of the cells. In this series of tests, the same suspensions of ATBS crystal suspensions A and C are supplied into the same rotating drum filter in which the cells have varying depths. The pressures applied are as follows.

The supply pressure in the filtration zone is 2.5 bars, the pressure in the washing zone is 4 bars, and the pressure in the drying zone is 8 bars.

The rotating drum has a rotational speed of 30 revolutions per minute. The filtration cells have a different depth and are covered by a polypropylene filter cloth with a mesh opening of 50 μm.

The analysis results on the cakes obtained are given in Table 9.

TABLE 9

Analysis results on cakes obtained with rotary filter technology with variable cell depth.

| ATBS crystal suspension | Cell depth (mm) | Moisture of crystals obtained (%) | IBSA (ppm) | IBDSA (ppm) |
|---|---|---|---|---|
| A | 12 | 13 | 44 | 48 |
| A | 20 | 13 | 45 | 49 |
| A | 50 | 13 | 37 | 39 |
| A | 80 | 14 | 52 | 54 |
| A | 120 | 15 | 68 | 75 |
| A | 200 | 22 | 113 | 162 |
| C | 12 | 13 | 43 | 45 |
| C | 20 | 14 | 45 | 49 |
| C | 50 | 13 | 30 | 35 |
| C | 80 | 15 | 53 | 56 |
| C | 120 | 15 | 69 | 88 |
| C | 200 | 23 | 109 | 158 |

Tests with 5-mm cell depths were carried out but the results are not satisfactory because the productivity is strongly affected which makes the process not industrially sustainable.

These results show that an adjustment of the cell depth makes it possible to obtain a better purity of ATBS.

Example 3—Filtration with a Vacuum Belt Filter

The ATBS crystal suspensions A, C and E produced in Example 1 are supplied to a vacuum belt filter having a given filtration zone. The interior of the belt filter is maintained under a 300-mbar vacuum.

The vacuum belt filter is equipped with a polypropylene filter cloth having a mesh opening of 50 μm.

The cake formed on the filter is then conveyed to the washing zone.

A washing solution at a 1.5-bar pressure, containing 95% by mass of acrylonitrile and 5% by mass of water, is sprayed onto the cake.

A nitrogen gas stream, at a pressure of 2 bars, supplies the drying zone of the vacuum belt filter.

The cake thus washed and dried is then discharged using a scraper knife.

An analysis by liquid chromatography of the crystals obtained makes it possible to complete the residual contents of IBSA and IBDSA.

The experimental conditions of filtration tests 8 to 10 of suspensions A, C and E are recorded in Table 10. The analysis results on the cakes are recorded in Table 11.

TABLE 10

Experimental filtration conditions for suspensions A, C and E with vacuum belt filter technology.

| Filtration test | ATBS crystal suspension | Supply rate (kg/h) | Filter surface (m$^2$) | Filtration rate (kg/h/m$^2$) |
|---|---|---|---|---|
| 8 | A | 9000 | 23.9 | 377 |
| 9 | C | 3720 | 10.1 | 368 |
| 10 | E | 4000 | 10.8 | 370 |

TABLE 11

Analysis results on cakes obtained with vacuum belt filter technology.

| Filtration test | ATBS crystal suspension | Moisture of crystals obtained (%) | IBSA (ppm) | IBDSA (ppm) |
|---|---|---|---|---|
| 8 | A | 28 | 120 | 190 |
| 9 | C | 26 | 110 | 170 |
| 10 | E | 25 | 127 | 183 |

Example 4—Filtration with a Continuous Decanter with a Full Cylindrical-Conical Bowl The ATBS crystal suspensions A, B and F produced in Example 1 are supplied into a continuous decanter with a full cylindrical-conical bowl.

The bowl is rotated at a speed of 4,400 revolutions per minute, and the internal conveying screw is rotated at a speed of 4,420 revolutions per minute.

The cake formed inside the bowl is conveyed by the internal screw to the discharge zone. A solid bowl decanter does not allow washing the cake. Consequently, no washing of the cake is carried out.

An analysis by liquid chromatography of the crystals obtained makes it possible to complete the residual contents of IBSA and IBDSA.

The experimental conditions of filtration tests 11 to 13 of suspensions A, B and F are recorded in Table 12. The analysis results on the cakes are recorded in Table 13.

TABLE 12

Experimental filtration conditions for suspensions A, B and F with a continuous decanter with a full cylindrical-conical bowl.

| Filtration test | ATBS crystal suspension | Supply rate (kg/h) | Filter surface (m$^2$) | Filtration rate (kg/h/m$^2$) |
|---|---|---|---|---|
| 11 | A | 9000 | 21.5 | 419 |
| 12 | B | 4500 | 9.65 | 466 |
| 13 | F | 3000 | 6.89 | 435 |

TABLE 13

Analysis results on the cakes obtained with a continuous decanter with a solid cylindrical-conical bowl.

| Filtration test | ATBS crystal suspension | Moisture of crystal obtained (%) | IBSA (ppm) | IBDSA (ppm) |
|---|---|---|---|---|
| 11 | A | 54 | 375 | 450 |
| 12 | B | 48 | 366 | 419 |
| 13 | F | 63 | 398 | 459 |

The cakes obtained have a muddy appearance, they are difficult to transport with the solids conveying techniques known to a person skilled in the art.

Example 5—Filtration with a Continuous Decanter with a Cylindrical-Conical Bowl Having a Solid Bowl Zone and a Perforated Bowl Zone In filtration test No. 14, crystal suspension A supplies a cylindrical-conical bowl continuous decanter having a solid bowl zone and a perforated bowl zone. The total surface of the bowl is 25 m² and the perforated bowl zone has a mesh size of 500 μm.

The supply rate of the crystal suspension is 9,000 kg/h.

The bowl is rotated at a speed of 4,400 revolutions per minute, and the internal conveying screw is rotated at a speed of 4,420 revolutions per minute.

The cake formed inside the bowl is conveyed by the internal screw to the zone of the perforated bowl. A washing solution at a pressure of 1.5 bar containing 95% by mass of acrylonitrile and 5% by mass of water is supplied and sprayed onto the cake.

The cake obtained has an acrylonitrile residual moisture of 65% by mass, and a muddy appearance. The cake is difficult to transport with the solids conveying techniques known to a person skilled in the art.

In addition, 50% of the cake has passed through the filter and is found in suspension in the liquid filtrate. This represents a direct loss, and therefore yield, of 2-acrylamido-2-methylpropane sulfonic acid.

Analysis by liquid chromatography of the crystals obtained shows that the latter have an IBSA content of 300 ppm and an IBDSA content of 280 ppm.

The filtration rate of the crystal suspension is 498 kg/m²/h.

In conclusion, these examples show that the filtration process according to the invention makes it possible to obtain 2-acrylamido-2-methylpropane sulfonic acid crystals having much lower levels of IBSA and IBDSA than those obtained with other filtration processes. Thus, the process according to the invention provides a continuous process making it possible to significantly improve the purity of the 2-acrylamido-2-methylpropane sulfonic acid crystals while retaining excellent filtration performance and residual moisture in acrylonitrile of the crystals. Furthermore, it should be noted that this improvement is accompanied by an increase in the filtration rate, and therefore in productivity.

The invention claimed is:

1. A continuous process for filtering a suspension of 2-acrylamido-2-methylpropane sulfonic acid crystals by means of a rotary pressure filter equipped with a drum, a surface of which is provided with cells covered with a filter medium, said drum rotating within a fixed concentric cylinder comprising at least three zones sealed from each other, respectively a filtration zone, a washing zone and a discharge zone, each zone opening onto the cells, the process comprising the following steps:
   a) supplying the filtration zone with a suspension of 2-acrylamido-2-methylpropane sulfonic acid crystals and filtering said suspension in the cells until a cake is formed,
   b) supplying the washing zone with a washing solution and washing the cake formed in the cells,
   c) discharging the washed cakes from the cells at the discharge zone; and wherein, a depth of the cells covering the filter medium is between 6 and 150 mm and in that a pressure of between 1 and 10 bars is applied in the filtration and washing zones.

2. The process of claim 1, wherein, the depth of the cells is between 10 and 100 mm.

3. The process according to claim 1, wherein, the process comprises the following steps:
   a) supplying the filtration zone under pressure with a suspension of 2-acrylamido-2-methylpropane sulfonic acid crystals and simultaneously filtering said suspension in the cells until a cake is formed,
   b) supplying, under pressure, the washing zone with a washing solution and simultaneously washing the cake formed in the cells.

4. The process of claim 1, comprising at least one of the following two additional steps:
   between step b) and step c), drying the washed cake by injecting gas into a drying zone;
   after step c), washing the cells in a cleaning zone before resuming a filtration cycle.

5. The process of claim 4, wherein, a pressure is applied at least in the filtration, washing and drying zones, the pressure being different from one zone to another.

6. The process of claim 5, wherein, the pressure applied in the filtration zone is between 1.1 and 9 bars.

7. The process of claim 5, wherein, the pressure applied in the washing zone is between 1.1 and 9 bars.

8. The process of one of claim 5, wherein, the pressure applied in the drying zone is between 1.1 and 10 bars.

9. The process of claim 1, wherein, in step b) the washing is carried out with a solution containing at least 90% by mass of acrylonitrile.

10. The process of claim 4, wherein, the gas is at a temperature between 10° C. and 150° C. in the drying step.

11. The process according to claim 1, wherein, the suspension of 2-acrylamido-2-methylpropane sulfonic acid crystals comprises between 10 and 30% by mass of crystals of 2-acrylamido-2-methylpropane sulfonic acid.

12. The process of claim 1, wherein, the rotational speed of the drum is between 2 to 60 revolutions per minute.

13. The process of claim 1, wherein, a supply rate of the suspension of 2-acrylamido-2-methylpropane sulfonic acid crystals is between 1 m³/h and 30 m³/h.

14. The process of claim 1, comprising a drying step of the cake discharged until 2-acrylamido-2-methylpropane sulfonic acid crystals are obtained.

15. The process of claim 1, wherein, a cake of 2-acrylamido-2-methylpropane sulfonic acid crystals is obtained.

16. The process of claim 1, wherein, the cake of 2-acrylamido-2-methylpropane sulfonic acid crystals, comprising less than 60 ppm of IBSA and strictly less than 60 ppm of IBDSA.

17. The process of claim 1, wherein, 2-Acrylamido-2-methylpropane sulfonic acid crystals are obtained.

18. The process of claim 1, wherein, a polymer is obtained from 2-acrylamido-2-methylpropane sulfonic acid crystals obtained.

19. An oil or gas recovery process comprising the preparation of an injection fluid containing the polymer obtained according to claim 18 and the injection of said fluid in an underground formation.

20. The process of claim 1, wherein, the depth of the cells is between 15 and 70 mm.

* * * * *